United States Patent
Hartmann et al.

(10) Patent No.: US 6,554,965 B1
(45) Date of Patent: *Apr. 29, 2003

(54) RECTIFICATION COLUMN FOR ISOLATING PURE SUBSTANCES FROM HIGH BOILING AIR-AND/OR TEMPERATURE SENSITIVE SUBSTANCES

(75) Inventors: Horst Hartmann, Böhl-Iggelheim (DE); Wolfram Burst, Mannheim (DE); Wulf Kaiser, Bad Dürkheim (DE); Harald Laas, Maxdorf (DE); Paul Grafen, Weisenheim (DE); Bernhard Bockstiegel, Römerberg (DE); Kai-Uwe Baldenius, Frankenthal (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/466,844

(22) Filed: Dec. 20, 1999

Related U.S. Application Data

(62) Division of application No. 08/981,491, filed on Jan. 8, 1998, now Pat. No. 6,111,117, which is a continuation of application No. PCT/EP96/02850, filed on Jun. 29, 1996.

(30) Foreign Application Priority Data

Jul. 8, 1995 (DE) ........................................ 195 24 928

(51) Int. Cl.[7] ............................ B01D 3/00; B01D 47/00
(52) U.S. Cl. ............. 202/158; 159/43.1; 159/DIG. 42; 202/262; 202/269; 261/DIG. 72; 261/112.2; 62/643

(58) Field of Search .................................. 202/158, 259, 202/267.1, 262, 269; 261/112.2, DIG. 72; 159/43.1, DIG. 42; 62/640, 643; 203/2, 100; 549/413

(56) References Cited

U.S. PATENT DOCUMENTS

| | | | | |
|---|---|---|---|---|
| 4,186,159 A | * | 1/1980 | Huber | 261/112 |
| 4,455,339 A | * | 6/1984 | Meier | 261/DIG. 72 |
| 4,471,014 A | * | 9/1984 | Den Hartog et al. | 261/DIG. 72 |
| 4,950,430 A | * | 8/1990 | Chen et al. | 261/112.2 |
| 4,981,621 A | * | 1/1991 | Pluss | 261/112.2 |
| 5,132,056 A | * | 7/1992 | Lockett et al. | 261/112.2 |
| 5,188,773 A | * | 2/1993 | Chen et al. | 261/112.2 |
| 5,454,988 A | * | 10/1995 | Maeda | 261/112.2 |
| 5,644,932 A | * | 7/1997 | Dunbobbin et al. | 62/640 |
| 5,653,126 A | * | 8/1997 | Harada et al. | 202/158 |
| 5,730,000 A | * | 3/1998 | Sunder et al. | 62/643 |
| 5,950,454 A | * | 9/1999 | Burst et al. | 62/643 |

* cited by examiner

Primary Examiner—Virginia Manoharan
(74) Attorney, Agent, or Firm—Oblon, Spivak, McClelland, Maier & Neustadt, P.C.

(57) ABSTRACT

A reflection column which contains liquid distributors having at least 500 drip points/m$^2$, which are arranged at an angle of about 90° C. to cloth layers of packing elements located immediately therebelow; and a combination of insulation and protective heating. The column is advantageously used for the rectification of mixtures of high-boiling air- or temperature-sensitive substances requiring effective separation efficiency.

9 Claims, 3 Drawing Sheets

Figure 1:
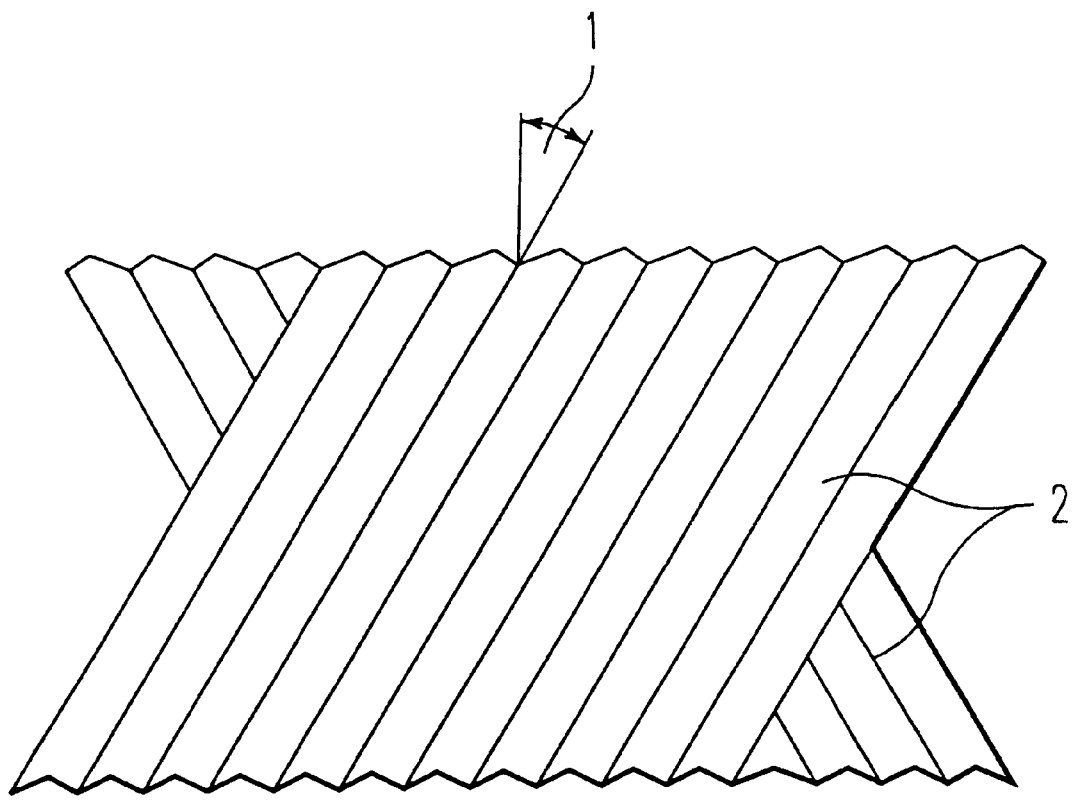

RECTIFICATION COLUMN FOR ISOLATING PURE SUBSTANCES FROM HIGH BOILING AIR-AND/OR TEMPERATURE SENSITIVE SUBSTANCES

This is a Division of application Ser. No. 08/981,491, filed on Jan. 8, 1998, U.S. Pat. No. 6,111,117 which is a continuation of international application PCT/EP 96/02852, filed Jun. 29, 1996.

The invention relates to a process for isolating pure substances from mixtures of high-boiling air- and/or temperature-sensitive substances which require a high separation efficiency by rectification under medium vacuum, in particular a process for the rectification of crude vitamin E acetate, for the purpose of purifying from lower-boiling and higher-boiling impurities, and to columns suitable for this process.

FIELD OF THE INVENTION

The workup of product mixtures by distillation generally affords the best results in the case of countercurrent distillation (also called rectification), ie. a specific distillation process with a countercurrent of reflex flowing downwards and vapor flowing upwards in rectification columns. The rectification columns normally used for this purpose are such that the mixture to be separated is introduced into the middle part of the column, and the vapor on its way through the column from the bottom to the top becomes enriched in more volatile components while the reflux from top to bottom becomes enriched in less volatile components. Mass and heat transport is intensified by elements fitted inside the column, such as column plates or packings, which ensure a sufficient contact time of the phases and a sufficiently large phase boundary area. However, these column internals, together with the reflux flowing downwards, result in a resistance in the column which is called the pressure drop. The pressure drop in a column depends not only on the nature and amount of the compounds to be rectified but also very strongly on the nature of the column internals.

Generally used for the fractionation of high-boiling substance mixtures which require a high separation efficiency are rectification columns which have packings which are built up systematically in regular geometry and have defined areas for the countercurrent phases to pass through, because packings with a regular structure are distinguished in comparison with random packings by the possibility of higer flow rates and a better separation effect, and have a lower specific pressure drop and a smaller required packing volume and thus also a smaller necessary mass and heat exchanging height. They are therefore used in all vacuum rectifications in which, because of the temperature-sensitivity of the mixture to be separated, it is particularly important to limit the pressure drop in the column.

Particularly suitable column packings are metal cloth packings of the BX and CY types supplied by Sulzer (cf. Sulzer company publication "Trennkolonnen für Distillation and Absorption") and metal cloth packings with a similar effect supplied by other companies such as Montz GmbH.

A diagrammatic representation of such columns is to be found, for example, on page 103 of the textbook "Thermische Trennverfahren" by Klaus Sattler, VCH Verlagsges.mbH, Weinheim (FRG), 1988. Concerning further details of the rectification of substance mixtures, we refer to this textbook by Klaus Sattler, pages 101–225, in particular 120–160 and 199–214.

The highest product temperature occurs in the bottom of a column. Apart from the overhead pressure, it is closely determined by the pressure drop from the column internals derived from the required separation efficiency. In rectification columns, the bottom temperature is not significantly affected by reducing the overhead pressure to less than 0.5 mbar.

The thermal stressability of many high-boiling mixtures is so low that, despite the use of the described metal cloth packings with ordered structure and overhead pressures in the column of only required for the necessary separation efficiency would result in bottom temperatures which are above the decomposition range for the compounds to be separated. This is why to date the fractionation of such mixtures by distillation has generally been carried out in the high vacuum range (about $10^{-1}$ to $10^{-5}$ mbar), ie. short-path distillations or molecular distillations are used. However, in the case of mixtures with low relative volatilities it is possible to obtain high purities only with low yields in these distillations.

One example of a mixture of high-boiling and highly air- and/or temperature-sensitive substances which require a high separation efficiency is synthetic vitamin E acetate (VEA) which is prepared industrially by reacting trimethylhydroquinone with phytol or isophytol and subsequently esterifying with acetic anhydride, and still contains small amounts of colored lower-boiling and higher-boiling impurities. Since VEA is increasingly being used in the human diet and for health prophylaxis, the demands on the purity of this product are increasing. Rectification, which is very advantageous in general for purification of products on an industrial scale, is very difficult with VEA owing to its high boiling point together with its instability at higher temperatures. This is why to date essentially distillations under high vacuum or even molecular distillations have been carried out in order to be able to distill VEA at the lowest possible temperatures.

Despite the use of high vacuum ($10^{-1}$ to $10^{-5}$ mbar), the purities obtained in the prior art are generally only 97.3% (cf. DE 2 743 920), 98% (cf. DE 42 08 477 and JP-B-58 011 869), 98.5% (cf. U.S. Pat. No. 3,459,773) or 98.5 to 99% (cf. DE 2 160 103). Purities above 99% have been obtained only by molecular distillation, namely purities of 99.3% according to JP-A 51/14671 and 99.5% according to JP-A-62/226976, although it should be noted that the products obtained in this way would presumably show lower purities on investigation with the more accurate analytical methods in use now and with purer comparison substances. In addition, the yields which can be obtained in such distillations are in each case rather low.

However, since distillations under high vacuum, but especially molecular distillations, while giving high purities not only have the disadvantage of low distillation yields but are also extremely costly in terms of the capital costs and in terms of the operating costs, it was object of the invention to develop a process for the separation by distillation of high-boiling air- and/or temperature-sensitive substances which require a high separation efficiency, in which high-vacuum distillation or molecular distillation is unnecessary, ie. a process in which an overhead pressure of from 0.1 to 2 mbar is sufficient and thus considerably less costly pressure-reducing processes are necessary and a high distillation yield is obtained.

It was an object of the invention in particular to find a process for the final purification of VEA by distillation able to result in colorless VEA with a primary of 99% or more and good distillation yields even by rectification under medium vacuum in columns containing metal cloth packings with ordered structure.

The invention thus relates to a process for isolating pure substances from mixtures of high-boiling air- and/or temperature-sensitive substances which require a high separation efficiency by rectification under medium vacuum in columns containing metal cloth packings with ordered structure, which comprises carrying out the rectification in a mass transfer column in which a) the liquid distribution is undertaken with channel distributors with 500 or more drip points/m$^2$, preferably 900 to 1200 drip points/m$^2$, b) in which the channels of the distributors are arranged at an angle of about 90° to the cloth layers of the packing elements located immediately below the distributor, c) in which 2 or more packing elements which have a height of from 20 to 100 mm and whose cloth layers are in each case rotated by 90° with respect to one another are located immediately below the liquid distributors, d) the column is designed so that virtually no heat exchange through the column wall can take place during the rectification, and e) for air-sensitive substances, the column is designed so that it is possible to operate virtually with exclusion of air.

The process according to the invention takes place particularly advantageously when the cloth packings used are such that the angle of inclination of the serration of the individual cloth layers of the packing to the column axis is as small as possible in order to minimize the specific pressure drop of the packing.

Whereas the angle of inclination of the serration is generally 30° with the usual Sulzer BX packings, the cloth packings preferred in the process according to the invention are those whose angle of inclination of the serration of the cloth layers to the column axis is from 0 to 25°, preferably 3 to 10°. The angle of inclination of the serration of the cloth layers to the column axis is illustrated in FIG. 1. In this Figure, 1 means the angle of inclination of the serration of the cloth layers to the column axis and 2 means cloth layers.

The process according to the invention is particularly important for the final purification of VEA, ie. in the case where the mixture of high-boiling air- and/or temperature-sensitive substances rectified is a VEA contaminated with colored, lower being and higher-boiling substances.

Taking the example of the purification of VEA, the developments in apparatus and process technology of the process according to the invention are to be explained in detail hereinafter.

Columns can be operated industrially at a cost which is still acceptable with overhead pressures of from 0.5 mbar. At a pressure of 1 mbar, VEA has a boiling point of about 240° C. The limited thermal stability of VEA means that the temperature at the bottom of the column is limited to about 260–270° C. A rectification column must therefore be operated with a maximum bottom pressure of only 4 mbar. This means that a pressure drop of only about 3–3.5 mbar between top and bottom of the column can be tolerated. This is very difficult to achieve because a separation efficiency of about 10 to 30 separation stages is necessary for final purification of the VEA, and a pressure drop of from 0.3 to 0.5 mbar per separation stage must normally be expected. In the operating ranges according to the invention there were no measurement available on the pressure drops.

According to feature a) of the main claim, a liquid distribution with channel distributors with 500 or more drip points is claimed. Distributors which are similar but circular and are also called capillary distributors are marketed by the companies Sulzer and Montz and are described, for example, in EP 512 277. Known channel distributors generally have only 50 to 60 drip points per m$^2$.

The use according to the invention of the channel distributors brings about a reduction in the pressure drop in 2 different ways. They result, on the one hand, in a rapid and extremely fine distribution and thus eventually in better utilization of the packing for distribution of the mixture to be separated and, on the other hand, in a very low trickling density. The lower limit of liquid flow rate stated for Sulzer packaging of the BX type is about 0.2 m$^3$/m$^2$·h. Through the use, according to the invention, of the channel distributors with 500 or more, preferably 900 to 1200, drip pints with VEA the liquid flow rates achieved in the process according to the invention are only 0.03–0.3 m$^3$/m$^2$·h overhead and 0.03–1.0 m$^3$/m$^2$·h in the stripping part of the column. It has been found, surprisingly, that even with such low liquid flow rates the complete wetting of the metal packings, which is required for optimal separation efficiency, is ensured. This low trickling density means that the gas flow rate in the column and thus the pressure drop is extremely low.

However, to obtain an optimal separation efficiency it is important not only to have a large number of drip points but also to arrange the distributors having regard to the packing elements.

One layer of a cloth packing generally consists of a multiplicity of, usually single, cloth layers which are 170 mm high. Each packing layer is, when fitted, rotated by in each case 90° in relation to the previous layer. The distributors are likewise arranged rotated by 90° in relation to the packing element located immediately below the distributors, or to the packing layer located there.

The liquid now spreads out on one of these cloth layers at a particular angle. After an inflow length which depends on the spreading angle and the distance between two drip points, a uniform film has formed over a cloth layer.

Optimal utilization of the packing, ie. the fastest possible distribution of the liquid on all cloth layers, is achieved when the packing is rotated by 90° at this point.

Hence, according to the invention, 2 or more packing elements with a height of from 20 to 100 mm, preferably 25 to 50 mm, in particular 35 to 45 mm, whose cloth layers are in each case rotated by 90° with respect to one another are used underneath the liquid distributors. The separation of the packing into elements of small height means that the fastest possible distribution and thus optimal utilization of the packing for the separation can be achieved. By contrast, in the conventional arrangement of packing, the inflow length is about 340 mm, which means that with a packing height of 2 meters about 17% of the packing are not fully utilized for the actual separation operation.

According to feature e), the rectification is to be carried out virtually with exclusion of air.

Laboratory tests have shown that, for example, in the case of VEA at the high temperatures required for the rectification even the slightest leaks in the distillation equipment result in the product darkening in color, which cannot be tolerated because of the high demands on quality. The use of newly developed, particularly high quality sealing materials such as Helicoflex® supplied by Cefilac for sealing flanges and/or openings for devices to monitor the process is therefore absolutely necessary. It is particularly advantages to seal flanges by using welded lip seals as described, for example, in German Patents DE 27 10 859, DE 39 12 478 or DD 44 07 728.

As already explained, only small mass flows circulate in the medium vacuum rectification columns according to the invention. Thus every loss of heat immediately leads to uncontrolled condensation on the column wall, which reduces the separation efficiency of the column. The preventing of heat exchanges through the column wall can best be ensured by a combination of insulation and protective heating of the column.

Such protective heating is advantageously achieved industrially in the following way: a metal plate jacket is attached on a first insulating layer on the column jacket. This metal plate jacket is insulated again. Another metal plate jacket and the heating are finally insulated toward the outside. The heating is then controlled in such a way that the temperature difference between the column jacket and the first metal plate jacket is zero.

For the final purification of VEA according to the invention it is necessary to operate the rectification with overhead pressures of from 0.2 to 1 mbar, preferably 0.5 to 1 mbar, and with bottom pressures of from 1 to 4 mbar, preferably 1.5 to 3.5 mbar, in particular 2 to 3 mbar.

In the rectification of VEA according to the invention, the packed columns are operated with a liquid flow rate of from 0.03 to 0.3 $m^3/m^2 \cdot h$ in the concentrating part of the column and with a liquid flow rate of from 0.03 to 1.0 $m^3/m^2 \cdot h$ in the stripping part of the column.

Figure 2A:
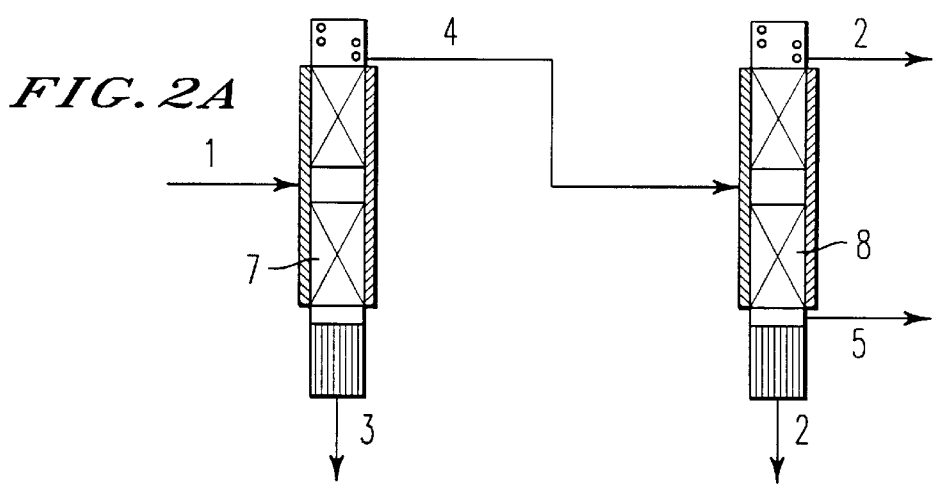
Figure 2B:
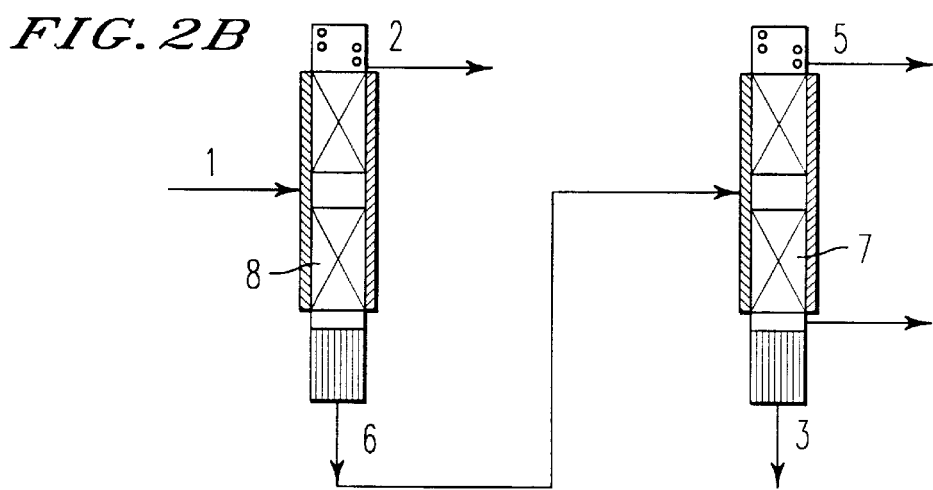

In general, and also for VEA, 2 columns are necessary to remove coloring lower-boiling impurities and higher-boiling impurities. FIGS. 2a and 2b depict diagrammatically 2 possible distillation concepts for the rectification of VEA in 2 packed columns. The meanings in these are 1 inlet for crude vitamin E acetate
2 outlet for feed quality
3 outlet for feed quality+residue
4 outlet distillate
5 outlet for food or drug quality, ie. purity>99%
6 bottom stream
7 rectification to remove high boilers
8 rectification to remove low boilers.

However, it is also possible to use equivalent distillation facilities such as a baffle plate column. A baffle plate column is, in general, a combination of 2 separate column packings within an outer column jacket on which inlet and side discharge are located.

Figure 2C:
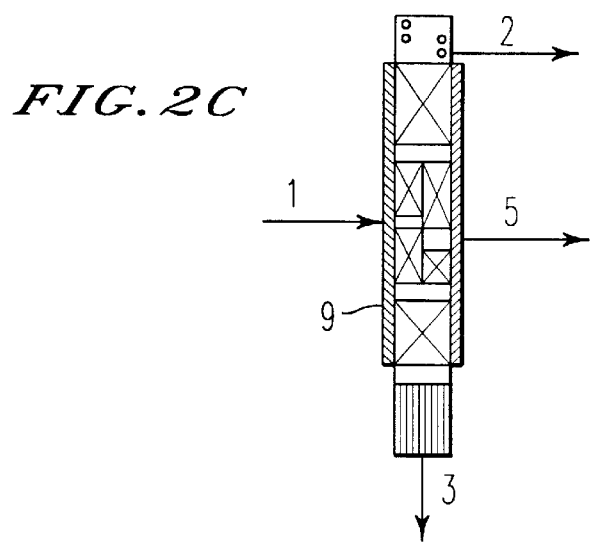

Such a baffle plate column is depicted diagrammatically in FIG. 2c. In this, 1, 2, 3 and 5 have the same meanings as in FIGS. 2a and 2b, and 9 means a baffle plate column.

The invention also relates to the packed columns equipped for the process according to the invention and to the use thereof for the final purification of impure VEA by rectification in the pressure range from 0.1 to 2 mbar.

These are packed columns with a stripping part and concentrating part containing metal cloth packings with ordered structure, each of which are rotated by 90° with respect to one another, for the rectification of mixtures of high-boiling air and/or temperature-sensitive substances which require a high separation efficiency, with overhead pressures of from 0.1 to 2 mbar, wherein, a) they contain channel distributors with 500 or more drip points/$m^2$ as liquid distributors, preferably 900 to 1200 drip points/$m^2$,
b) the channels of the liquid distributors are arranged at an angle of 90° to the cloth layers of the packing elements located immediately below the distributor,
c) they contain 2 or more packing elements which have a height of from 20 to 100 mm and whose cloth layers are in each case rotated by 90° with respect to one another below the liquid distribution,
d) they contain a combination of insulation and protective heating, which ensures that virtually no heat loss through the column wall can take place during the rectification, and
e) the seals and flanges are designed so that virtually exclusion of air is ensured.

Figures 3A, 3B:
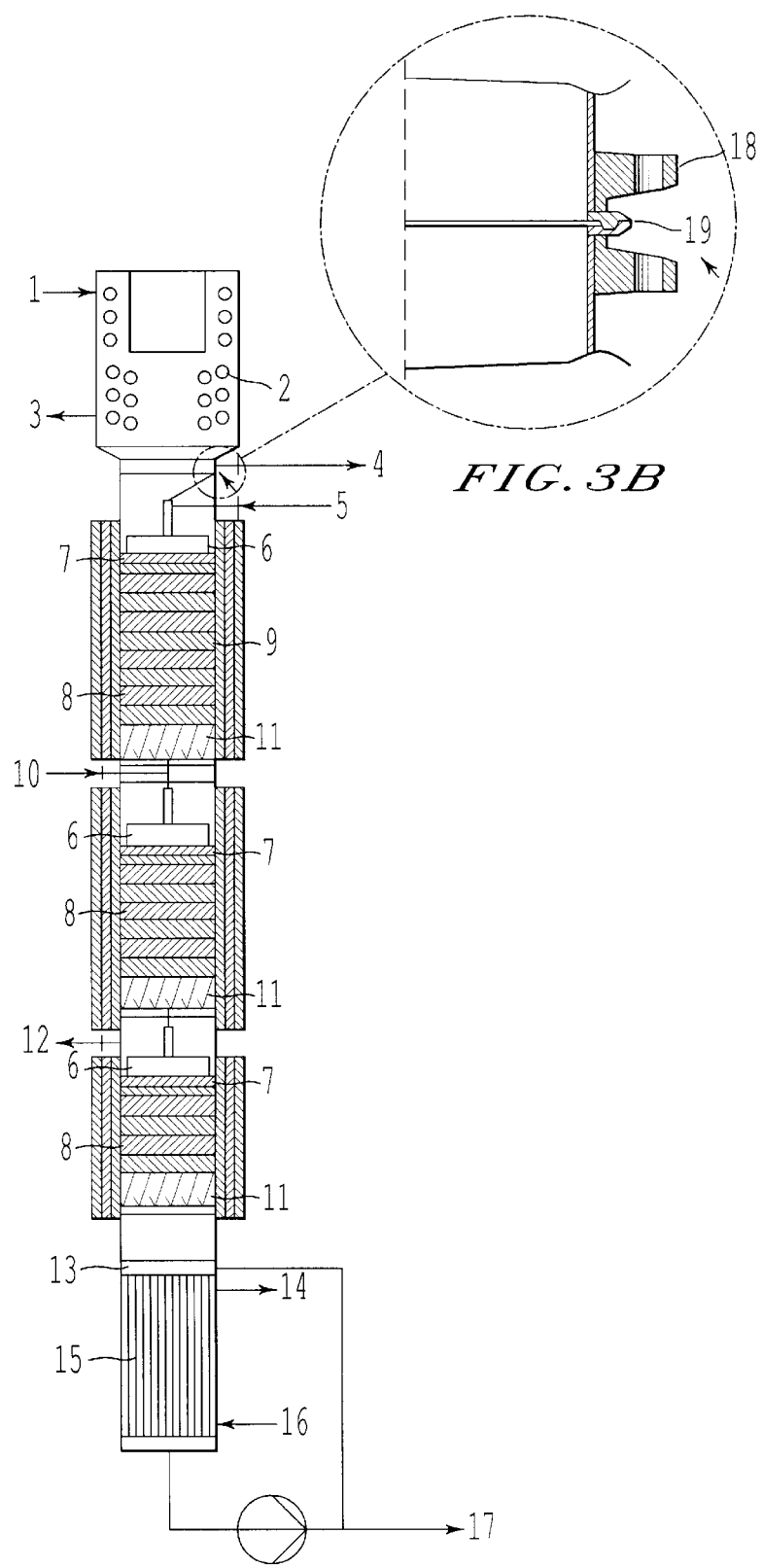

A packed column which can be used according to the invention for the rectification of VEA is depicted diagrammatically in FIG. 3.

The meanings in this are:

1 inlet for cooling medium
2 condensor
3 outlet for cooling medium
4 distillate
5 reflux
6 channel liquid distributors with 500 to more drip points/$m^2$
7 packing elements with a height of from 20 to 100 mm
8 packing elements with a height of about 170 mm
9 a combination of insulation and a protective heating
10 inlet for crude VEA
11 liquid collector
12 side discharge
13 sealing element
14 outlet for heating medium (exit)
15 falling film evaporator
16 inlet for heating medium (entry)
17 bottom discharge
18 flanges
19 seals It is possible with the aid of the packed columns according to the invention and of the process according to the invention to rectify mixtures of high-boiling air- and/or temperature-sensitive substances which require a high separation efficiency, such as crude VEA or mixtures of tocopherols with impurities, also under medium vacuum, ie. pressures of from 0.2 to 2 mbar, preferably 0.5 to 1 mbar, in columns with cloth packings with low pressure drop and with very good distillation yields.

Description, by way of example, of the process for purifying crude vitamin E acetate by the distillation concept shown in FIG. 2a.

Degassed, synthetic crude vitamin E acetate with a content of about 96% VEA is introduced at from 200 to 250 degrees Celsius through the inlet 10 into the middle of the first rectification column containing a height of from 3 to 5 m of packings of the Sulzer BX of Montz A3 type. The liquid is distributed uniformly over the cross-section of the column at the top and at the inlet to the column by the newly developed high-efficiency channel distributors 6. The packing elements 7 with a height of from 20 to 100 mm are located underneath the newly developed channel distributors. The cloth layers of the packing elements arranged immediately below the channel distributors 6 are rotated by an angle of 90° with respect to the channels of the liquid distributors. The column is equipped with a protective heating 9 and is operated adiabatically. Flanges and connections are provided with welded lip seals or high quality metal seals.

The overhead pressure of the column is from 0.5 to 1 mbar. The reflux ratio is from 2 to 4. The liquid flowing back in the column is at from 170 to 220 degrees Celsius. From 5 to 20% of the inlet stream are removed at the bottom of the column.

The overhead product at from 200 to 250° C. from the first column is delivered into the middle of the second rectification column containing a height of from 3 to 5 m of packings of the Sulzer BX or Montz A3 type. The liquid is distributed over the column cross-section at the head and at the inlet by the newly developed high efficiency channel distributors. This column is also equipped with a protective heating and is operated adiabatically. Flanges and connections are provided with welded lip seals or high quality metal seals.

The overhead pressure of the column is about 0.5 mbar. The reflux ratio is from 5 to 15. The liquid flowing back into the column is at from 170 to 220° C. From 5 to 20% of the inlet stream are removed at the top and bottom of the column. The vitamin E acetate removed in the side discharge directly above the vaporizer of the second column is virtually colorless (color number less than 2) and is of drug quality with a purity of more than 99%. The yield of product with this purity is about 50% of theory.

The residue taken from the bottom of the first rectification column is separated in a thin-film evaporator under a pressure of from 1 to 5 mbar. The distillate obtained in this way can, like the overhead and bottom products from the second column, be sold as vitamin E acetate for animal feed purposes (feed quality). These products generally contain from 90 to 99% VEA. The total distillation yield of feed and drop quality VEA is from 95 to 98%.

We claim:

1. A rectification column which comprises:
   a) channel liquid distributors with at least 500 drip points/m$^2$ as liquid distributors;
   b) the channel liquid distributors being arranged at an angle of about 90° C. to cloth layers of packing elements located immediately below the channel liquid distributors;
   c) 2 or more of the packing elements immediately below the channel liquid distributors which have a height of from 20 to 100 mm and whose cloth layers are in each case rotated by 90° with respect to one another;
   d) a combination of insulation and a protective heating, which ensures that virtually no heat loss through the column wall occurs during rectification; and
   e) seals and flanges which are designed to virtually exclude air in the rectification column.

2. The column of claim 1, wherein the liquid distributors comprises 900 to 1,200 drip points/m$^2$.

3. The column of claim 1, wherein the packings have an angle of inclination of the serration of the layers to a column axis of from 0 to 25°.

4. The column of claim 3, wherein said angle of inclination is from 3 to 10°.

5. The column of claim 1, wherein the seals are welded lip seals.

6. The column of claim 1, wherein said 2 or more packing elements have a height of from 25 to 50 mm.

7. The column of claim 6, wherein said 2 or more packing elements have a height of from 35 to 45 mm.

8. The column of claim 1, which is adiabatically operable.

9. The column of claim 1, wherein said protective heating is effected by a first metal plate jacket which is attached on a first insulating layer on a jacket of the rectification column, wherein said metal plate jacket is also insulated by a second insulating layer, and another metal plate jacket and a heating device are attached to the second insulating layer, and the heating device is insulated toward the outside, whereby during heating a temperature difference between the column jacket and the first metal plate jacket is zero.

* * * * *

UNITED STATES PATENT AND TRADEMARK OFFICE
CERTIFICATE OF CORRECTION

PATENT NO.     : 6,554,965 B1                                          Page 1 of 1
DATED          : April 29, 2003
INVENTOR(S)    : Hartmann et al.

It is certified that error appears in the above-identified patent and that said Letters Patent is hereby corrected as shown below:

<u>Title page,</u>
Item [62], Related U.S. Application Data, should read:
-- Related U.S. Application Data

[62] Division of application No. 08/981,491, filed on Jan. 8
    1998, now Pat. No. 6,111,117, which is a continuation
    of application No. PCT/EP96/02852, filed on Jun. 29, 1996. --

Signed and Sealed this

Sixteenth Day of September, 2003

JAMES E. ROGAN
*Director of the United States Patent and Trademark Office*